United States Patent [19]
Kryger et al.

[11] 4,218,142
[45] Aug. 19, 1980

[54] MASK ANALYSIS

[75] Inventors: David L. Kryger, Chelmsford; R. William Killam, Tewksbury, both of Mass.

[73] Assignee: Aerodyne Research, Inc., Bedford, Mass.

[21] Appl. No.: 884,606

[22] Filed: Mar. 8, 1978

[51] Int. Cl.² ............................................. G01N 21/32
[52] U.S. Cl. .................................. 356/394; 250/563; 250/572; 356/431; 356/239
[58] Field of Search ................. 356/71, 430, 431, 444, 356/239, 394; 250/548, 563, 572

[56] References Cited
PUBLICATIONS

Bruning et al., "An Automated Mask Inspection System—AMIS" IEEE Trans. on Electron Devices, vol. ED-22, No. 7, pp. 487–495, 7/75.
Thomas, "Defect Scanner for Repetitive Patterns", IBM Tech. Discl. Bull., vol. 16, No. 10, p. 3158, 3/74.

Primary Examiner—John K. Corbin
Assistant Examiner—Matthew W. Koren
Attorney, Agent, or Firm—Frank A. Steinhilper

[57] ABSTRACT

Masks used in the production of integrated circuits are analyzed and tested by a scanning spot from a laser beam comparing the position signal of the scan from a mask against a data base representing another mask which may be selected at random. Apparatus includes a laser, means to form and scan a minute spot from said laser, an x-y stage to move a mask under the scan, a detector, and means to compare scan results.

9 Claims, 3 Drawing Figures

MASK ANALYSIS

BACKGROUND OF THE INVENTION

In the production of integrated circuits it is usual to prepare a mask comprising a number of dies, usually several hundred dies arranged in regular rows and columns on a mask. To produce such a mask the design for a single layer of circuit is produced, ordinarily from a drawing, painting, or the like, and ordinarily relatively large in size. At the present time, this circuit usually comprises a number of lines laid down in the proper design and generally may comprise this design in the form of a thin pattern of chromium or other material coated on the surface of a transparent carrier such as a glass slide or the like. The design generally is produced by photo-etch methods.

The first design usually exists in a relatively enlarged size, called a reticle, and is used as the master for projection by means of a step-and-repeat camera onto a transparent surface which will become the mask. Ordinarily, this mask also is formed by photo-etch methods, and the step-and-repeat camera performs the exposure step of such photo-resist procedure to position the dies in precise positions on the mask. Typically, several hundred reduced sized replicas of the original pattern will be formed in precise orientation and location on the mask surface. As a consequence of photo-resist processing there is formed the mask comprising a transparent surface, such as a piece of glass having several hundred dies on its surface, each die corresponding to an exact reduced sized replica of the original reticle.

To produce complete integrated circuits this mask and similar ones are used as masters for laying down individual layers of patterns, one on top of the other in precise position and orientation. Thus, each mask is used in combination with others to form several hundred completed integrated circuits. Such integrated circuits are then employed to form complex electronic equipment. While partial inspection of masks is generally carried out, the complexity is such that many mask defects are not detected during inspection. At the present time, in process inspection is unreliable or overly time-consuming and performance inspection cannot be done until manufacture of the integrated circuit is completed.

Heretofore, the testing of masks has generally been done individually by visual examination. A skilled worked looks at a mask through a microscope, or perhaps at a projection of the microscope image on a CRT display, to detect breaks in the lines of the mask, bulging lines which may touch other lines, or other mask defects. It is estimated that perhaps 25% or more of an entire production force may be engaged in such examination and testing and that such testing may, even so, fail to detect all or even most of the flaws, even though they actually are visible.

As a result of these limitations on inspection, there can be serious inefficiencies or reduced product yield resulting in the waste of many man hours of labor and many hours of wasted time for manufacturing equipment.

GENERAL NATURE OF THE INVENTION

A mask is tested for defects in the individual dies by a scanning system that covers all areas of all dies on the mask to identify defects and to designate their location in a defined area in the designated die. The individual dies are located on the mask in precisely positioned columns and rows making possible easy identification of an individual die and also making possible precise location identification within a die. A fine optical spot (which may be as fine as or finer than 0.75 microns in each direction) is moved repeatedly in the x-direction while the mask is translated in the y-direction. The optical spot transmits through the mask in the clear areas and is interrupted by lines on the mask, and the transmitted beam is detected. The entire mask is then moved in the x-direction to a new location, ordinarily the like position in the next column of dies, and the scanning of a column of scan lines is repeated. Data corresponding to a single die, which may be selected at random from the dies on the mask, are stored in a memory data base and such data are compared with the data from scanning each column in each die. The data are examined in a comparator. The comparison designates first whether there is a difference between the scanning data and the data base, and if there is a difference, designates the physical location of the difference and the sign of the difference as to whether there is an opaque area in the die not matched by an opaque area in the data base, or a transparent area in the die not matched by a corresponding transparent area in the data base. If desired, one can designate the type of defect, identifying the defect as a hole, a chrome deposit, a tear or the like.

In use and operation, the individual scan length is preferably several hundred microns so that a scanning column is several hundred microns across the surface of the mask. Thus the scanning of a single die may consist of several columns or as many as a couple dozen columns using today's most frequent mask designs. In a preferred mode of operation a first column is scanned through the leading edge of a first column of dies on the mask and the mask is then stepped directly to the leading edge of the second column of dies on the mask which is then scanned. The leading edge of each column of masks is scanned successively, after which the mask is moved to a second position in the first column of dies. In this manner it is not necessary to empty and reload the data base until after the corresponding scan on all of the dies in a mask. A typical mask having an active area of about $2\frac{1}{2}$ inches square can be scanned in less than ten minutes, and a large mask having an active area of about 5 inches square can be scanned in less than 40 minutes. In the scanning process the probability of detection of defects 0.75 microns in diameter or larger is virtually 100% and detection of defects as small as 0.5 microns is quite possible, but with reduced probability.

The invention is more fully disclosed in the accompanying drawings in which.

SPECIFIC DISCLOSURE OF THE INVENTION

Figure 1:
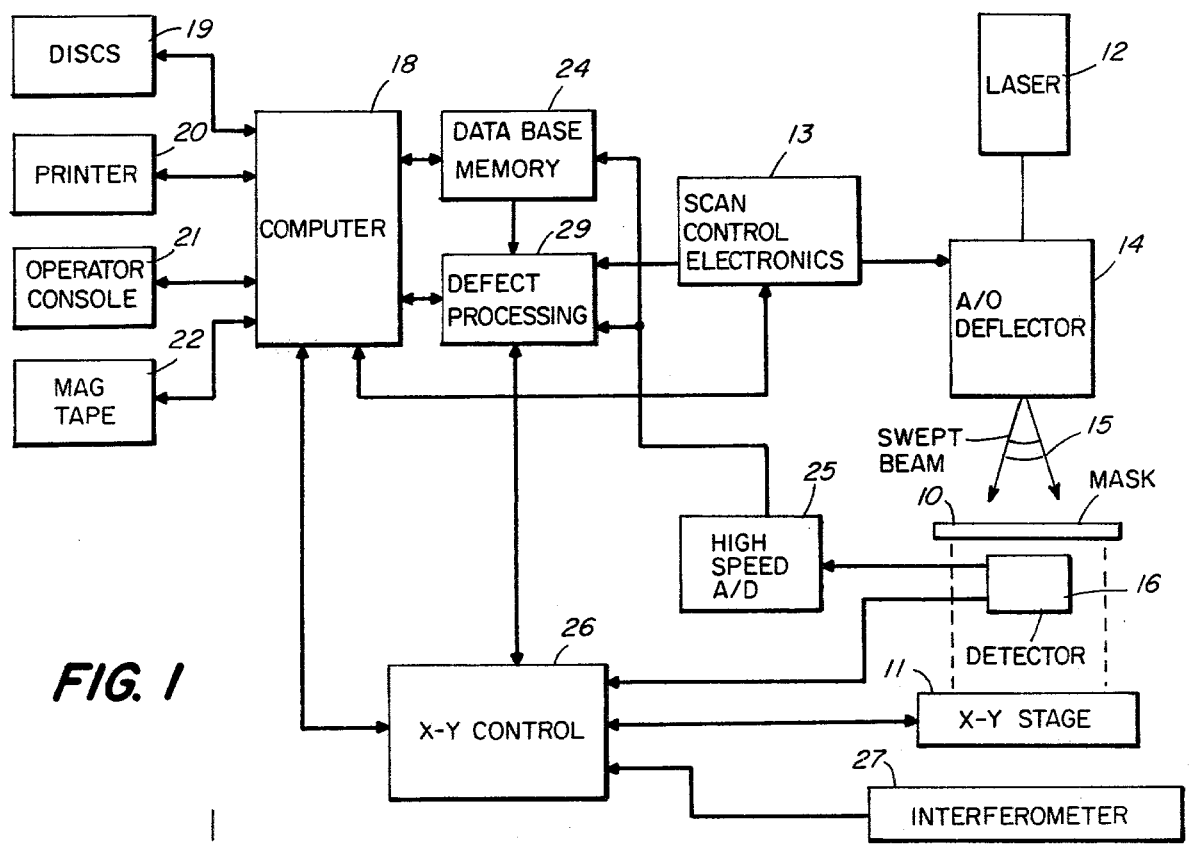
FIG. 1 is a block diagram in outline of mask analysis system according to one embodiment of the invention.

In FIG. 1 is illustrated in outline a system for mask analysis. As shown therein a mask 10 is positioned on an x-y stage 11 or other mechanism for controlled movement of a mask separately in the y-direction and the x-direction to permit moving the entire area of mask 10 into and through an analysis zone. A laser 12 with an acousto-optical (A/O) deflector 14 controlled by scan control means 13 sweeps a controlled and very fine laser beam 15 onto and across a portion of mask 10 on stage 11. Positioned under stage 11 is a detector 16 to receive a laser beam when it passes through mask 10 and to generate an electric signal therefrom. This signal is then used and analyzed in the system as indicated hereinafter.

A computer 18 is disposed to receive input data, operating instructions, and the like from stored data such as discs 19, and an operator console 21. In connection with each of these devices information may be fed into the computer or information from the computer may be fed into the device. An operator console 21 is provided to monitor the analysis, and results can be recorded on a printer 20 or on a tape device 22.

A data base memory 24 is operatively connected to receive data from computer 18 and to submit data to computer 18. The data base memory also received input data from a high speed A/D circuit 25 which in turn receives data from detector 16.

An x-y control device 26 controls x-y stage 11 for moving the mask 10 through the desired operational positions and sequences. This x-y control device receives input from computer 18 and from a two-axis interferometer 27 positioned near the stage 11.

A defect processing device 29 is connected to receive original data from data base memory 24, to receive position data from the x-y control 26, and to receive mask data from detector 16 through the high speed A/D circuit 25. It also is positioned and connected to receive scan data from scan control device 13. In this manner it perceives detected information together with x-y position information. It also receives master information from the computer and data base to permit comparison between mask data and standard data for an ideal mask. It can thus recognize absorption or transmission data for the laser beam through mask 10 as being the same as or different from data base memory 24. It indicates agreement or opposition of sign of such data and identifies the location both as to the individual die on the mask and as to the scan location within such die area, and if desired can identify a type of die defect.

Figure 2:
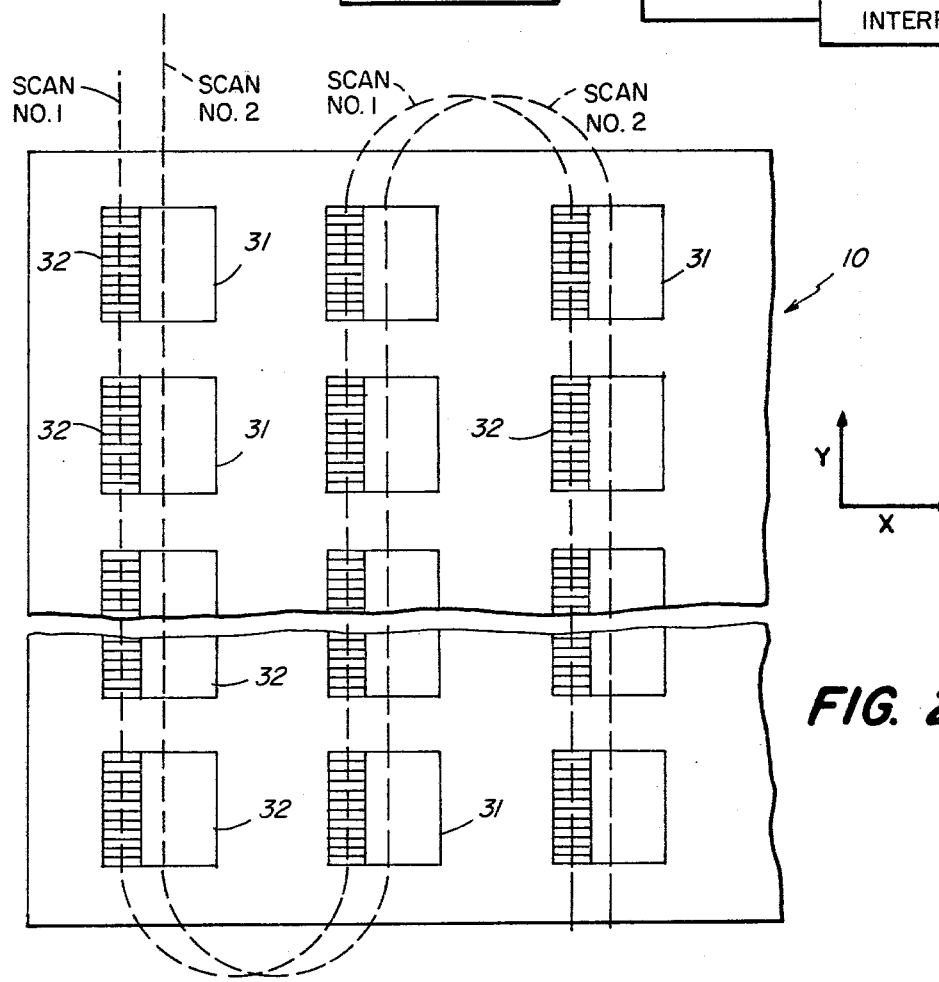
FIG. 2 is a diagram of scanning paths over a mask.

In FIG. 2 is illustrated the scanning path along a mask 10 according to one presently preferred embodiment of the invention. A mask 10 having thereon a multiplicity of individual dies 31 arranged in precise rows and columns is scanned in paths indicated by scan No. 1 and scan No. 2. In scan No. 1 the scanning beam 15 moves in the x-direction at the leading edge of a first column of dies 31. A multiplicity of individual bars 32 illustrated along the leading edge of the first column of dies corresponds to the scanning action of x-y stage 11 in cooperation with the acousto-optic deflector 14 or swept beam 15. This beam 15 sweeps or scans in the x-direction while the x-y stage 11 is moved in the y-direction. Then the beam 15 sweeps again in the same direction along the x-direction. In both theory and practice the scan can begin at one edge of its path, cross the path and snap back to begin its next scan; or it can scan back and forth in both x-directions. At the present time a design decision has been made to scan in only the one direction, at least partly because the fastest and most reliable acousto-optical deflector operates in that mode. This continuous scanning is repeated through the position of a first die 31, and then is repeated along the leading edge of a next die, and in succession the entire first column of such dies 31. Then the x-y stage 11 is moved one column width to bring the beam 15 in position along the leading edge of the next column. The deflection of the beam 15 in the x-direction is continued and the x-y stage 11 is moved backward along the leading edge of the second column (to cause the scanning to move in the upward direction of FIG. 2).

After the scanning of the leading edge of column 2 is complete the stage is translated to column 3 and the scan is once again carried out in the original y-direction. This same scanning action is carried out across the entire width of the mask until the leading edge of every die has been scanned. The x-y stage 11 then returns to the first column, and advances one position as indicated for scan No. 2. Scan No. 2, in the same pattern as scan No. 1, then scans a second area of each die 31. While the x-y stage 11 is returning to its position to start the new scan, the data base memory may be replaced (or refilled) with the correct data base for scan No. 2. After scan No. 2 is complete across the mask, the stage 11 returns to its position for scan No. 3 and the data base memory is refilled with the appropriate new data. According to one embodiment of the invention the data base for each of these scans may be the data from the first die 31 in the top left-hand corner of the mask 10. If desired the data base memory may be loaded with the appropriate data from any other die 31 chosen by plan or selected at random, or it may be loaded with the original computer data utilized to form the first reticle from which the dies are derived.

At the present time, continuous motion scanning and translation of the x-y stage 11 is preferred, rather than stepping motion, in order to achieve maximum accuracy and throughput. Position is determined from the interferometer readout and from the deflection of the acousto-optical deflector beam. The defect processor 29 also designates the die position, identifying which die is being studied or which die contains a defect.

Figure 3:
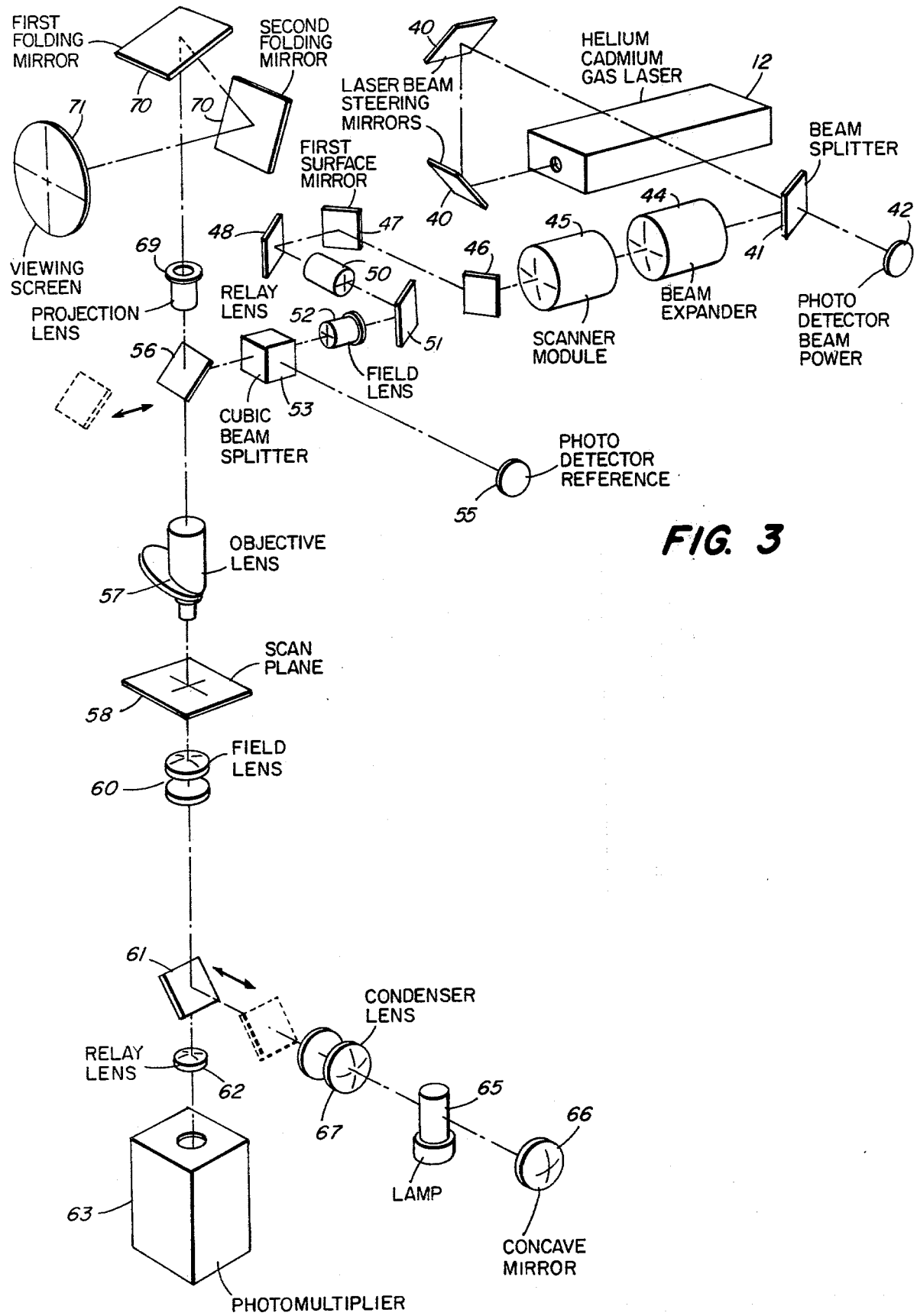
FIG. 3 is a diagram of the optical system for apparatus according to one embodiment of the invention.

FIG. 3 shows an optical system wherein a light beam from a laser 12 is directed to a scanning module 45 and focused into a fine scanning spot at a scan plane 58 and directed to a detector such as a photomultiplier 63. In a presently preferred embodiment of this invention the laser 12 is a helium-cadmium laser at 0.4416 mn, and lenses or other elements transmitting the beam into its path to the photomultiplier should be accurate at this wave length.

Positioned near the laser 12 are one or more laser beam steering mirrors 40 steering the beam to a beam splitter 41. The transmitted beam goes to a photo detector 42 for beam power measurement, and the reflected beam to beam expander 44.

From the beam expander 44, the beam goes to a scanning module 45 which provides accurate, controlled deflection to the beam, and then to mirrors 46, 47 and 48, and thence through a relay lens 50. A next mirror 51 directs the beam to a field lens 52 and to a cubic beam splitter 53. One beam from beam splitter 53 is directed to a reference photo detector 55 and another beam from the splitter is directed to a first movable mirror 56. Reference photo detector 55 provides reference levels for photomultiplier 63 to assist in adjustment or calibration. When mirror 56 is in position it directs the laser beam to objective lenses 57 which focus the beam on scan plane 58 at which is positioned the x-y stage (see FIG. 1).

Positioned beyond the scan plane is a field lens 60 through which the beam passes to a second movable mirror 61. When mirror 61 is out of position the beam passes to a relay lens 62 and photomultiplier 63. A lamp 65 and a concave mirror 66 direct a beam from the lamp through condenser lenses 67 to mirror 61. When mirror 61 is in position and mirror 56 out of position the beam from lamp 65 and, optionally, with one or more folding mirrors 70, the beam is directed to a viewing screen 71. As can be seen, when mirror 56 is in position and mirror 61 is out of position, the apparatus is in the operating mode, and the beam from laser 12 is directed through scan plane 58 to detector or photomultiplier 63. When the positions are reversed, with mirror 61 in position and mirror 56 out of the beam path, a beam from lamp 65 reaches the viewing screen to permit operator viewing of a mask. Desirably, laser 12 is shuttered while the apparatus is in the projection or monitor mode.

The x-y stage 11 is a device to support and move the mask 10 at accurately controlled speeds in the x-direction and the y-direction and may, if desired, be specifically constructed for this mask analysis apparatus. Various such devices are commercially available, however, and one device actually employed is made by Yosemite Laboratories Berkeley, Cal., Modified 9606-5.

In use and operation the apparatus shown in the figures is employed for the extremely rapid analysis and testing of masks for the production of integrated circuits. A mask ordinarily comprising several hundred dies arranged in regular columns and rows on a substrate is placed on the x-y stage 11 of the apparatus. A spot from laser 12 is scanned across the mask in the pattern illustrated in FIG. 2. The signal from the detector corresponding to one of the dies is employed as information in the data base and as a matter of ease and convenience, the die selected for such comparison preferably is the first one scanned by the spot. If desired, any of the dies may be selected at random for this purpose, and in the alternative the data base may comprise information from an original computer store corresponding to a circuit or pattern being produced, or may be taken directly from the original reticle or other source. The data read from the scanning of a mask are compared on a real time basis and when an inconsistency between the data for the mask (a die on the mask) and the data in the data base are observed, the information may be presented to the operator. Alternatively, it may be stored in a computer or printed or stored on magnetic tape with information which may include the location of the die in which the inconsistency exists and the position within the die of the inconsistency.

The inconsistency detected can be identified not only as to location but also as to sign. In other words, it can be determined, and the operator informed whether the inconsistency represents an additional area of transparency in a specific die or an additional area of opaque nature in the die. Thus, it is possible to tell whether there is a break in the line, a bulge or displacement in a line, or simply an extra spot of opaque deposit on a die. Experience can determine whether a bulge or additional deposit is within or outside normal tolerances. In the alternative the data will inform the operator the location of the inconsistency and he can examine the mask visually at the correct location to make a judgment as to the extent of the inconsistency.

Manual controls (not shown) can be provided to position the mask at a desired location on the x-y stage 11 so that the spot from lamp 65 can enable the operator to make such examination as is required. The operator can, in this matter, determine whether the inconsistency is beyond tolerance and also whether the inconsistency is correctable.

By means of the apparatus of the present invention a mask having an active mask area of about 2½ inches square can be examined in about 9 minutes and a mask having an active area of about 5 inches square can be examined in about 37 minutes. The examination is virtually 100% reliable as compared with present visual methods which frequently are less than 25% reliable.

At the present time, the focused laser spot or pixel is about 0.75 mn in diameter and the trend in technology is such that it is reasonably expected that the spot definition can be increased to a pixel about 0.5 mn in diameter. Accordingly, the present state of optics technology will accomodate current integrated circuit production and it is reasonably anticipated that it will continue to accomodate integrated circuit production throughout the forseeable future.

We claim:

1. Apparatus for determining the location and nature of mask defects in masks for the production of integrated circuit, wherein said masks include a repetitive multiplicity of individual miniature-sized dies of like design and configuration arranged in regularly spaced rows and columns on said mask comprising:
   a laser;
   means to focus the beam of said laser to a fine spot of a size in the order of the size of defects being sought;
   means to deflect said beam to move said spot repeatedly in a path in a first direction substantially parallel with the rows of dies between a first deflection starting point and a second deflection termination point;
   mounting means to mount a mask to interrupt said laser beam at the focal point of said spot;
   means to move said mounting means carrying said mask at a predetermined rate of motion in a second direction at approximately right angles to said first direction, said second direction being substantially parallel with the columns of dies on said mask;
   means to move said mounting means a predetermined distance in said first direction, said means being controlled to move said mask in said first direction by the distance between columns of dies;
   detection means to detect the transmitted laser beam passing through said mask;
   means to store a first position-dependent record corresponding to a record of the transmitted laser beam passing through one of said dies on said mask;
   means to compare said stored record against each of a multiplicity of position-dependent signals, each signal corresponding to the transmission of said laser beam through an individual die on said mask.

2. The apparatus of claim 1, wherein differences between a first position-dependent record and a second position-dependent record are identified as to location of said laser spot on said mask with respect to identifying the row and column of said location and the scan and step position of said location within the area of said die.

3. Apparatus according to claim 1, wherein said first position-dependent record corresponds to a record of transmission of said laser beam of a die selected at random from said mask.

4. Apparatus according to claim 1, wherein said first position-dependent record corresponds to a record of transmission of the first of said dies positioned to be scanned by said beam.

5. A method of analyzing integrated circuit production masks to detect minute inconsistencies therein, each of said masks comprising a multiplicity of substantially identical dies arranged in regular columns and rows, said dies having transparent and opaque areas corresponding to portions of electrical circuits on a transparent substrate, said method comprising:
 a. focusing a laser beam in an original location at a focal plane in a spot approximately the size of inconsistencies to be detected;
 b. mounting a mask at said focal plane, said mask being movable in said plane in both the x and y directions, the x-direction corresponding to the direction of rows of dies on said mask and the y-direction corresponding to the direction of columns of dies on said mask;
 c. scanning said spot at a predetermined rate and in a path of predetermined width across said focal plane in the x-direction;
 d. moving said mask in the y-direction to cause said spot to scan a band of a single column of said dies;
 e. moving said mask in the x-direction a distance equal to the distance between columns of dies and repeating step d to cause said spot to scan the corresponding band of another column;
 f. repeating steps e and d to cause said spot to scan the corresponding band of each of the columns of said multiplicity of dies;
 g. thereafter returning said spot to a next section of a column of dies removed from said original location by the width of one band and repeating steps c, d, e and f;
 h. and repeating step g successively until the entire area of each die is scanned;
 i. detecting the laser spot transmitted through the transparent substrate throughout steps c through h, and determining the position pattern of said spot being transmitted through said transparent substrate and of said spot impinging on opaque die areas;
 j. and comparing the pattern corresponding to one of said dies against the pattern corresponding to each of the others of said dies to detect inconsistencies therebetween.

6. The method of claim 5 wherein the selection of a position pattern corresponding to one of said dies for comparison against other dies is a random selection.

7. The method of claim 5 wherein the position pattern selected for comparison against other position patterns is the pattern corresponding to the die located in the first row and the first column of said dies on said mask.

8. The method of claim 5 wherein the position pattern selected for comparison against other patterns corresponds to a position pattern for an original from which all of said dies are produced.

9. A method of analyzing integrated circuit production masks, each of said masks comprising a multiplicity of substantially identical dies arranged in columns and rows to detect minute inconsistencies in said dies, said dies corresponding to portions of electrical circuits and consisting of optically transparent and opaque areas corresponding to said portions of electrical circuits, said method comprising scanning each of said dies with a laser beam focused in a spot approximately the size of inconsistencies to be detected to determine a position pattern corresponding to said pattern of transparent and opaque areas for each of said dies, selecting a pattern corresponding to one of said dies and comparing said selected pattern against the patterns corresponding to each of the others of said dies, and observing differences between said patterns to determine the existence of inconsistencies between one pattern and another, whereby to detect flaws in said patterns of transparent and opaque areas of said dies.

* * * * *